United States Patent
Capart

(10) Patent No.: US 10,220,010 B2
(45) Date of Patent: *Mar. 5, 2019

(54) LYOPHILIZED MESNA COMPOSITIONS

(71) Applicant: AuXin Surgery SA, Louvain la Neuve (BE)

(72) Inventor: Gilles Capart, Brussels (BE)

(73) Assignee: AUXIN SURGERY SA, Louvain la Neuve (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/871,573

(22) Filed: Jan. 15, 2018

(65) Prior Publication Data

US 2018/0133176 A1     May 17, 2018

Related U.S. Application Data

(62) Division of application No. 15/701,873, filed on Sep. 12, 2017, now Pat. No. 10,111,844, which is a division of application No. 15/108,934, filed as application No. PCT/EP2015/050047 on Jan. 5, 2015, now abandoned.

(30) Foreign Application Priority Data

Jan. 6, 2014   (EP) ..................................... 14150189

(51) Int. Cl.
    *A61K 9/19*         (2006.01)
    *A61K 31/10*        (2006.01)
    *A61K 47/26*        (2006.01)
    *A61K 31/185*       (2006.01)

(52) U.S. Cl.
CPC .............. *A61K 31/185* (2013.01); *A61K 9/19* (2013.01); *A61K 31/10* (2013.01); *A61K 47/26* (2013.01)

(58) Field of Classification Search
CPC .................................. A61K 31/10; A61K 9/19
See application file for complete search history.

(56) References Cited

U.S. PATENT DOCUMENTS

| | | | |
|---|---|---|---|
| 4,959,215 | A | 9/1990 | Sauerbier et al. |
| 5,227,373 | A | 7/1993 | Alexander et al. |
| 5,750,131 | A | 5/1998 | Wichert et al. |
| 2005/0124589 | A1 | 6/2005 | Roessler |
| 2016/0324809 | A1 | 11/2016 | Capart |
| 2018/0000759 | A1* | 1/2018 | Capart ................. A61K 9/1682 |

FOREIGN PATENT DOCUMENTS

| | | |
|---|---|---|
| EP | 0334083 A1 | 9/1989 |
| EP | 0538858 A1 | 4/1993 |
| WO | WO 2005/032515 A1 | 4/2005 |

OTHER PUBLICATIONS

Denaro et al. "Effectiveness of a mucolythic agent as a local adjuvant in revision lumbar spine surgery" Eur. Spine J. 2008, vol. 17, pp. 1752-1756. (Year: 2008).

Mashiach et al., "Mesna: a novel renoprotective antioxidant in ischaemic acute renal failure," *Nephrology Dialysis Transplantation*, vol. 16(3), pp. 542-551 (2001).

* cited by examiner

*Primary Examiner* — Joseph R Kosack
(74) *Attorney, Agent, or Firm* — Knobbe Martens Olson & Bear LLP

(57) ABSTRACT

A sterile lyophilizate composition having improved stability and shelf-life. The lyophilizate includes from 30 to 100% of Mesna and 0 to 70% of an excipient. A process for the preparation of the sterile lyophilizate composition and a dosage unit formulation including the lyophilizate composition.

8 Claims, No Drawings

LYOPHILIZED MESNA COMPOSITIONS

RELATED APPLICATIONS

This application is a divisional of U.S. patent application Ser. No. 15/701,873, filed Sep. 12, 2017, which is a divisional of U.S. patent application Ser. No. 15/108,934, filed Jun. 29, 2016, which is the U.S. National Phase under 35 U.S.C. 371 of International Application No. PCT/EP2015/050047, filed Jan. 5, 2015, which claims priority to European Patent Application No. 14150189.0, filed Jan. 6, 2014, the entire contents of which are incorporated herein by reference.

FIELD OF THE INVENTION

The present invention relates to sterile lyophilized compositions and a process for the preparation of said compositions. In particular, the invention relates to sterile lyophilized form of sodium-2-mercaptoethane sulfonate and to a process for its preparation. Said sterile lyophilized composition can be used for chemically assisted surgery and other applications.

BACKGROUND

Sodium 2-mercaptoethanesulfonate, hereinafter referred to as Mesna, has been widely used for several applications mainly as drug and/or formulations in the medical filed. For instance, Mesna has been used as prophylactic agent in reducing the incidence of hemorrhagic cystitis. Mesna has also been used as a mucolytic agent. Additionally, Mesna has been used in surgery, wherein it is known that when applied at a cleavage plane, Mesna breaks the molecular bonds between tissue layers, thereby facilitating tissue separation. Specifically, Mesna breaks disulfide bonds of polypeptide chains and proteins.

Mesna is a white hygroscopic powder with a characteristic odor. The liquid solution in water is highly sensitive to oxidation and rapidly decomposes on contact with oxygen to form di-Mesna also called disulphide Mesna, which is poorly absorbed, particularly in a humid atmosphere.

Most pure Mesna dosage forms used until today are liquid formulations. Since Mesna is very sensitive to oxidation and reacts in the presence of oxygen to form di-Mesna, the aqueous solutions have to be protected against oxygen. In addition, Mesna in liquid form is highly prone to oxidation in presence of metals. Therefore, Mesna solutions are usually sealed into glass ampoules, preferably in low iron glass containers under nitrogen blanket with stabilizers, antioxidants and metals chelating agents. Said glass containers are rather expensive. Furthermore, in some procedures, Mesna solutions are needed at different concentrations from those readily available in commercial glass vials, making the use of said vials tedious or inadequate.

When being used, the practitioner has to transfer the solution from glass containers to delivery device or to tube in order to incorporate the solution in the desired application. This step increases the chances of oxidation and contamination of the Mesna solution thereby having reduced Mesna activity or reduced sterility when used, for example in chemically assisted surgery.

Mesna is also available as a more stable crystalline powder from the synthesis (technical Mesna), but this form is not sterile and therefore not suitable to medical applications.

The object of the invention to overcome at least part of the above mentioned problems. The invention aims at providing sterile lyophilized Mesna compositions. This object is achieved in accordance with the invention by a composition and a process as indicated in the claims.

SUMMARY

In a first aspect, the invention provides a lyophilizate composition having improved stability and shelf-life, the lyophilizate comprising from 30 to 100% of Mesna and 0 to 70% of an excipient and/or a buffering agent. The use of excipient and/or buffering agent is hence optional.

In a preferred embodiment, the excipient is selected from the group comprising mannitol, trehalosee, sucrose or any combination thereof.

In another aspect, the invention provides a process for the preparation of a lyophilizate composition having improved stability and shelf-life, which comprises preparing an aqueous solution containing from 30 to 100% of Mesna and 0 to 70% of an excipient, freezing said solution to a temperature of about $-40°$ C. and removing both nonadsorptively bound and adsorptively bound water by sublimation at a temperature between about $-40°$ C. and about $+28°$ C. and at a pressure between 200 and 10 Pa, preferably between 100 and 10 Pa, more preferably between about 93 and 13 Pa. Said aqueous solution is preferably sterilized by ultrafiltration prior to the freezing.

In another aspect, the invention provides a dosage unit formulation comprising the lyophilizate composition described above in a container of sufficient size to allow reconstitution with a solvent thereby giving a solution of desired Mesna concentration.

In another aspect, the present invention provides for the use of a sterile lyophilizate composition as described above and/or the use of a dosage unit formulation as described above for assisting surgery and/or for any other application wherein Mesna is employed. Said application includes and are not limited to Mesna formulations, treatment using Mesna as prophylactic agent or mucolytic agent.

The sterile lyophilizate compositions according to the embodiments of the invention demonstrate better storage stability and dissolution characteristics than previous formulations. The sterile lyophilizate compositions of the present invention demonstrate unexpected improvements in physical and chemical stability and in shelf-life over Mesna powder and Mesna liquid formulations. In addition, lyophilized Mesna possesses superior dissolution characteristics and enhanced appearance on storage than non-lyophilized Mesna powders. Lyophilized Mesna are easily and quickly dissolved in the used solvent, i.e. 10 to 15 seconds are required for obtaining the Mesna solution at the desired concentration. The freshly made Mesna solution can then be immediately delivered to a target thereby having a maximal Mesna activity at the target location.

Sterile lyophilized Mesna according to the present invention can be provided in containers suitable to be connected to a solvent source and/or to a surgical device. This minimizes external handling of Mesna thereby considerably reducing contamination risks, such as contamination risks during surgery. In addition, the prepared Mesna solution can be used shortly after dissolving the Mesna lyophilizate, thereby providing maximal Mesna activity at a target location when used for instance for assisting surgery.

More generally, the sterile lyophilizate compositions according to the present invention are highly stable. This allows prolonged conservation of Mesna for different use and applications. Lyophilized Mesna of the present invention is easy to store as its storage does not require particular conditions. This is advantageous compared to the currently available pharmaceutical Mesna which is stored in low iron glass under nitrogen blanket.

Lyophilized Mesna of the present invention further provides the user with the possibility to reconstitute sterile Mesna solutions with different desired concentrations according to the intended use. Concentrations higher than 20% can be obtained in this manner.

The sterile solid lyophilized Mesna of the present invention makes possible the reconstitution of a Mesna solution for a wide range of medical applications, including surgery. This is not achievable using the known technical Mesna powder available to date. Said technical Mesna powder is not sterile. In addition, it is difficult to obtain Mesna at a certain desired concentrations by diluting commercial Mesna solutions available to date. Said commercial Mesna solutions are indeed limited to 10% or 20%.

DETAILED DESCRIPTION

The present invention relates to lyophilized compositions and a process for the preparation of said compositions. In particular, the invention relates to sterile lyophilized Mesna compositions. In other terms, the present invention provides a novel form of Mesna which is sterile. Said sterile Mesna form is suitable for medical application including but not limited to surgery.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

In a first aspect, the present invention provides a lyophilizate composition having improved stability and shelf-life. The lyophilizate composition comprises from 30 to 100% of Mesna and 0 to 70% of an excipient. The presence of said excipient is hence optional. The composition might consist entirely of Mesna thereby obtaining Mesna in solid form. Said solid Mesna is sterile.

In a preferred embodiment, the lyophilizate comprises from 35 to 90% of Mesna and 10 to 65% of an excipient. In a preferred embodiment, the lyophilizate comprises from 40 to 80% of Mesna and 20 to 60% of an excipient. In a preferred embodiment, the lyophilizate comprises from 45 to 70% of Mesna and 30 to 55% of an excipient. The lyophilizate might comprise 55% of Mesna and 45% of an excipient.

In a preferred embodiment, the excipient is selected from the group comprising mannitol, trehalose, sucrose or any combination thereof. In a preferred embodiment, the excipient is mannitol. In a preferred embodiment, the excipient is trehalose.

In a preferred embodiment, the lyophilizate composition consists of Mesna. In a preferred embodiment, the lyophilizate composition consists of Mesna and mannitol. In a preferred embodiment, the lyophilizate composition consists of Mesna and trehalose. In a preferred embodiment, the percentages of each component are as indicated above.

The lyophilizate compositions of the present invention have improved stability and shelf life compared to technical Mesna. Said lyophilizate Mesna compositions are stable over a time period which is at least 1.1, preferably at least 1.3, more preferably at least 1.5, even more preferably at least 1.8, most preferably at least 2 times longer than the time period during which technical Mesna is stable. The lyophilizate Mesna compositions of the present invention are stable over a time period which is at most 4, preferably at most 3.5, more preferably at most 3, even more preferably at most 2.8, most preferably at most 2.5 times longer than the time period during technical Mesna is stable. Said stability is determined by measuring the amount of Mesna disulfide of the stored Mesna.

The lyophilizate compositions of the present invention have improved heat stability or temperature stability compared to technical Mesna. Said lyophilizate compositions are stable at high temperatures. Indeed, said the lyophilizate compositions are more stable than technical Mesna at 40° C. and at room temperature.

In another aspect, the present invention provides a process for the preparation of a lyophilizate composition having improved stability and shelf-life, which comprises freezing an aqueous solution containing from 30 to 100% of Mesna and 0 to 70% of an excipient, to a temperature of about −40° C. and removing both nonadsorptively bound and adsorptively bound water by sublimation at a temperature between about −40° C. and about +28° C. and at a pressure between 200 and 10 Pa, preferably between 100 and 10 Pa, more preferably between about 93 and 13 Pa. Said aqueous solution is preferably sterilized by ultrafiltration prior to the freezing. The process of the invention leads to a solid sterile form of Mesna.

In a preferred embodiment of the process, the excipient is selected from the group comprising mannitol, trehalose, sucrose or any combination thereof. In a preferred embodiment, the lyophilization is preceded by a microfiltration step.

The present invention has resulted from work undertaken to ascertain if physical properties, such as shelf-storage and temperature stability, could be improved in a lyophilized Mesna composition. The initial stage of this research involved the evaluation of the suitability of lyophilizate cakes formed by freeze-drying various Mesna and/or Mesna-excipient compositions. The person skilled in the art easily understands that said cakes are solid forms consisting of Mesna and/or Mesna-excipient mixture. In making said evaluations, certain characteristics of the lyophilizate cakes were observed including original shape, shrinkage or melt-back, coloration, homogeneity, morphology, firmness and crystallinity. The dissolution characteristics of prototypes were then determined and these included rate of dissolution, completeness of dissolution, and characterization of the resultant solution; e.g. clarity and color.

The second stage of the research involved short term accelerated stability studies of compositions selected on the basis of their performance in the first stage of research. Excipients that were tested but not advanced to stage two evaluation included lactose; polyvinylpyrrolidone (PVP); dextrose; sodium bicarbonate; sodium carbonate; and tartaric acid. Lyophilizate compositions having mannitol, trehalose, glycine or urea as primary excipients were selected for the stage two stability testing. Lyophilizate compositions with urea or glycine as the primary excipient yellowed and decreased in potency during short term stability studies carried out at 40° C. In studies conducted at ambient room temperature, 24°-27° C., chemical and physical stability for the urea or glycine lyophilizate compositions was maintained for about 30 weeks. After 1 year storage lyophilizate compositions with urea or glycine were yellowed. Lyophilizate compositions with mannitol or trehalose as the primary excipient showed no yellowing or significant potency loss during storage under all conditions studied.

In a preferred embodiment, slow freeze-drying process is used for preparing the Mesna lyophilizate compositions. This process results in minimization of shrinkage of the lyophilizate cake. The control of shrinkage and absence of yellowing for these Mesna lyophilizate compositions contribute to the enhanced appearance of the final lyophilized product. In order to produce these Mesna lyophilizate compositions, it was learned that by controlling both the rate of freezing of the solution prior to vacuum-drying, shrinkage problems were minimized.

The lyophilizate compositions of the present invention are prepared by dissolving Mesna, Mesna and mannitol or Mesna and trehalose, in water of suitable quality known to the person skilled in the art. These aqueous solutions will be comprised of Mesna and optionally at least one excipient. Preferably, said aqueous solutions comprise 30 to 100% of Mesna and 0 to 70% of an excipient. Said excipient might be Mannitol or trehalose. The aqueous solutions might also comprise 10 to 70%, preferably 15 to 60%, more preferably 20 to 50% by weight to water volume of Mesna. In a preferred embodiment, the aqueous solution further comprises 30 to 90% by weight to water volume of mannitol or trehalose. In addition, other pharmaceutically useful auxiliary materials, such as excipients, buffers, preservatives and the like; in lesser amounts may be added to the solution and not depart from the present invention. While water is the preferred solvent for the solution, it would be possible to use other pharmaceutically acceptable solvents.

The pre-lyophilization solution is purified in a conventional manner by filtration using microbial retentive filters and nitrogen gas for pre-filter pressure. Sterilization of the solutions is performed by ultrafiltration prior to the freezing. The filtration-sterilized solution is then aseptically filled into sterile containers for lyophilization as described above.

Following the filling operation, the containers are loaded into trays and shelf-frozen in the lyophilizer chamber to about −40° C. The frozen solution is then lyophilized in the following manner; initially, the shelf temperature is set at about 0° C. and the vacuum is maintained at about 67 Pa (0.5 torr) with the condenser temperature at about −60° C. or lower. After completion of the primary drying (generally, about 24 to 48 hours), the shelf temperature is raised to about 25° to 28° C. and the chamber vacuum is lowered to about 13 Pa (0.1 torr) or less. These drying conditions are continued until the residual moisture in the lyophilizate is reduced to a level whereby Mesna is chemically stable. Generally, the secondary drying requires an additional 24-36 hours.

In a preferred embodiment, the time required for performing the Mesna lyophilization process and obtaining Mesna lyophilizate compositions is comprised between 10 and 30 hours, preferably between 15 and 25 hours, more preferably between 16 and 20 hours, most preferably about 18 hours. In a preferred embodiment, Mesna lyophilizate compositions are obtained via a process devoid of secondary drying.

In another aspect, the invention provides a dosage unit formulation comprising the lyophilizate composition of the invention in a container of sufficient size to allow reconstitution with a solvent thereby giving a solution of desired Mesna concentration. The size of the container comprising said dosage unit formulation preferably allows the introduction of from 0.5 ml to 10 ml of solvent. In a preferred embodiment, a first solvent volume is introduced in the container comprising said dosage unit formulation. The lyophilizate composition is thereby first diluted in said first volume of solvent. The obtained first diluted lyophilizate composition might be afterwards transferred to another container comprising a second solvent volume. The sum of the first and the second solvent volumes is a total solvent volume that is used to dilute the lyophilized composition thereby providing the final desired Mesna concentration.

In a preferred embodiment, the dosage unit formulation consists of the lyophilizate composition of the invention. The water solutions can be adjusted to obtain the desired characteristics of the Mesna solution. For example sodium chloride and sodium hydroxide can be used to obtain the desired tonicity and acidity for surgical applications. Said formulations can also be used for any other Mesna applications.

The Mesna, Mesna-mannitol or Mesna-trehalose dosage unit formulation according to an embodiment of the invention contain between 300 mg and 100 g, preferably between 1 g and 70 g, more preferably between 2 g and 60 g, most preferably between 3 g and 50 g Mesna per unit. Larger sized dosage unit formulation of Mesna lyophilized compositions are also possible and are a further embodiment of the present invention. In a preferred embodiment, the dosage unit size is designed such as to provide Mesna solution at a concentration comprised between 5% and 50%. This means that the dosage unit size is suitable to receive a solvent volume in which lyophilized Mesna is dissolved thereby having a Mesna solution at a concentration comprised between 5% and 50%.

Preferably, the container is capable of maintaining a sterile environment such as a vial, a syringe or a bag capable of being hermetically sealed by a stopper means. While such containers are usually glass, generally type I glass; they may also be of other suitable polymer materials which do not interact with the lyophilizate components. The container might be provided with a closure. Said closure is typically a stopper and preferably a sterile rubber stopper or an equivalent which gives a hermetic seal, will also allow entry for the purpose of introduction of diluent such as sterile water for reconstitution of the Mesna solution.

In a preferred embodiment, the container containing the dosage unit formulation is made of plastic or glass. Preferably said container is sterile. In a preferred embodiment, the container is a flexible bag made of a fluid tight plastic material or from moister barrier plastic which prevents humidity and light in the single chamber. Said bag or plastic is preferably resistant to low temperatures, i.e. from −10 to −100° C.

In a preferred embodiment, said container is suitable to be connected, through connection means, to a solvent source and/or to surgical devices. Preferably, said solvent is suitable for dissolving the lyophilizate composition contained in the container. Preferably said solvent is a sterile physiological saline solution. The connection means can be any means known to the person skilled in the art.

In a preferred embodiment, the solvent is suitable for dissolving the lyophilizate composition. Preferably said solvent is a sterile physiological saline solution. In a preferred embodiment, the solvent volume is chosen such as the concentration Mesna solution is of from 5% to 50%, preferably of from 10% to 40%, more preferably from 15% to 30%, most preferably from 20% to 25% or any value comprised in between the mentioned ranges.

EXAMPLES

Aqueous Mesna solutions were prepared by dissolving 5 g, 3 g or 1 g of Mesna in 10 ml Water for Injection. For each Mesna concentration (5 g/10 ml, 3 g/10 ml and 1 g/10 ml), at least 30 solutions were prepared.

The solutions were first passed through a sterile prefilter and then a sterile 0.2 micron pore size membrane filter. The solutions were placed in falcon tubes which were then placed in suitable lyophilization equipment and cooled (shelf-frozen) to a temperature of about 40° C.

The lyophilizer condenser was then cooled to about −60° C. or lower and the lyophilizer chamber was evacuated to a pressure of about 67 Pa (0.5 torr—range of 0.3 to 0.7). Shelf heat temperature was set at about 0° C. to begin the drying process. Following primary drying of about 24 to 48 hours, the shelf temperature was raised in order to bring the product temperature to near +25° C. Lyophilization was then continued until a final product temperature of about 25° C. to 28° C. and a chamber pressure of not more than 26 Pa (0.2 torr) was reached. The total lyophilization time will vary but depending on the capacity of equipment, will generally be in the range of about 72 to 96 hours. Following completion of the lyophilization process, the vacuum was relieved by the aseptic introduction of sterile air and/or nitrogen. At this point the falcon tubes are closed by suitable caps.

The impurities levels of the lyophilized Mesna solution at different concentrations were very low as determined by HPLC. HPLC analysis was performed according to the Eur. Pharmacopeia.

The lyophilized Mesna was stored at two different temperatures: 40° C.±2° C. and at room temperature, i.e. 21° C.±2° C. The stored lyophilized Mesna was tested after different storage periods. The tests evaluated the appearance of the lyophilized Mesna (change in color, texture) and the impurities content of the lyophilized Mesna. The results are summarized in table 1.

TABLE 1 appearance test and impurities levels of lyophilized Mesna stored at different temperatures

| | Room temperature | | | | 40° C. | | | |
|---|---|---|---|---|---|---|---|---|
| | 30 d | 60 d | 90 d | 120 d | 30 d | 60 d | 90 d | 120 d |
| 1 g/10 ml | LI, NCA | LI, NCA | LI, NCA | LI, NCA | LI, NCA | LI, NCA | LI, NCA | LI, NCA |
| 3 g/10 ml | LI, NCA | LI, NCA | LI, NCA | LI, NCA | LI, NCA | LI, NCA | LI, NCA | LI, NCA |
| 5 g/10 ml | LI, NCA | LI, NCA | LI, NCA | LI, NCA | LI, NCA | LI, NCA | LI, NCA | LI, NCA |

LI = low impurities. Impurities levels were compared to the impurities levels of the freshly lyophilized Mesna and/or the Mesna powder
NCA = No appearance change The stability of lyophilized Mesna is in general evaluated by measuring and determining the percentage of Mesna disulfide which is considered the most sensitive marker.

Measurements of Mesna disulfide percentage were conducted for different Mesna lyophilizates made according to the present invention. The compositions of the tested Mesna lyophilizates comprised 125 mg or 250 mg of Mesna in 2 ml Water for Injection. Other tested Mesna lyophilizates compositions further comprised trehalose or Mannitol. The amount of trehalose or Mannitol was half of (50%), equal to (100%), 1.5 times (150%) or 2 times (200%) the amount of Mesna. The results showed that the Mesna disulfide percentage was similar, lower or slightly higher compared to the Mesna disulfide percentage measured for technical Mesna (Mena P) which is available on the market. Any slightly higher increase was of maximum 0.5% compared to the Mesna disulfide percentage measured for the pharmaceutical grade Mesna (Table 2).

As shown in Table 2, the Mesna disulphide percentage was always 3 or 4 times lower compared to the maximum Mesna disulphide percentage set by the United States Pharmacopeia and the Pharmacopée Européenne which is of 3%. In addition, the sum of Mesna disulphide percentage and other impurities percentage was also always lower than said maximum of 3%.

TABLE 2 impurities levels of lyophilizate Mesna compositions

| Composition | MESNA | Mesna disulphide | Other impurities |
|---|---|---|---|
| Mesna P | 98.82% | 1.03% | 0.15% |
| Mesna P | 98.80% | 1.00% | 0.20% |
| Mesna P | 98.96% | 0.85% | 0.19% |
| 125 mg Mesna* | 99.00% | 0.80% | 0.19% |
| 125 mg Mesna* | 98.93% | 0.88% | 0.19% |
| 250 mg Mesna* | 99.00% | 0.81% | 0.19% |
| 250 mg Mesna* | 99.00% | 0.81% | 0.19% |
| 250 mg Mesna + 150% Tre* | 98.90% | 0.91% | 0.18% |
| 250 mg Mesna + 100% Man* | 98.70% | 1.11% | 0.19% |
| 250 mg Mesna + 100% Man* | 98.77% | 1.05% | 0.18% |

TABLE 2-continued impurities levels of lyophilizate Mesna compositions

| Composition | MESNA | Mesna disulphide | Other impurities |
|---|---|---|---|
| 250 mg Mesna + 150% Man* | 98.81% | 1.00% | 0.19% |
| 250 mg Mesna + 150% Man* | 98.78% | 1.03% | 0.18% |
| 250 mg Mesna + 200% Man* | 98.85% | 0.96% | 0.18% |
| 250 mg Mesna + 200% Man* | 98.73% | 1.09% | 0.19% |

Mesna P = Technical non-lyophilized Mesna;
* = lyophilized compositions;
Tre = Trehalose;
Man = Mannitol;
100% = equal to the amount of Mesna;
150% = 1.5 the amount of Mesna;
200% = 2 times the amount of Mesna.

Mesna stability after lyophilization was also tested on lyophilizates stored at room temperature about 5 months. The composition of the tested lyophilizates was 500 mg of Mesna dissolved in 5 ml Water for Injection. The tests were performed in duplicate. The results showed excellent Mesna stability as there has been no significant variation in the content of Mesna disulfide impurity (Table 3).

TABLE 3

Mesna stability in Mesna lyophilizate stored for 5 months at room temperature

| | MESNA | Mesna disulphide | other impurities |
|---|---|---|---|
| Test 1 | | | |
| Before Lyo | 98.02% | 1.83% | 0.15% |
| After Lyo | 98.02% | 1.84% | 0.14% |
| 5 months after Lyo | 99.11% | 0.78% | 0.11% |
| Test 2 | | | |
| Before Lyo | 98.86% | 0.96% | 0.18% |
| After Lyo | 98.98% | 0.82% | 0.20% |
| 5 months after Lyo | 99.88% | 0.00% | 0.12% |

Lyo = lyophilization

The results summarized in table 3 show the high and excellent stability of Mesna after lyophilization according to the present invention.

In addition to the tests summarized in table 1, 2 and 3, a solubility test was performed after each storage time under the different tested temperatures, i.e. room temperature and 40° C. The solubility tests were compared to the solubility of Mesna powder and of Mesna freshly lyophilized. The results showed that the solubility of the stored lyophilized Mesna at different temperatures was similar to the solubility of the freshly lyophilized Mesna which was less than 10 seconds. The solubility of technical Mesna powder, so not lyophilized, was of from 15 to 20 seconds.

For commercial purposes, the Mesna lyophilized according to the present invention is weighed in containers to be commercialized. The containers can be any of the ones know to the person skilled in the art and/or as described above.

The pH of lyophilized Mesna reconstituted in 2 ml milliQ-Water was measured. The pH ranged from 5.5 to 5.85. For lyophilizate composition comprising Mesna, the pH was about 5.84. For lyophilizate composition comprising Mesna and an amount of Mannitol which is 50% of Mesna amount, the pH was about 5.77. For lyophilizate composition comprising Mesna and an amount of Mannitol which is equal to (100%) the Mesna amount, the pH was about 5.8. These results show that buffering is not required during Mesna lyophilization process.

Although the present invention has been described with reference to preferred embodiments thereof, many modifications and alternations may be made by a person having ordinary skill in the art without departing from the scope of this invention which is defined by the appended claims.

What is claimed is:

1. A lyophilizate composition having improved stability and shelf-life, the lyophilizate composition consisting of from 30 to 100% of Mesna and optionally an excipient and/or buffering agent.

2. The lyophilizate composition according to claim 1, wherein the composition comprises an excipient and wherein the concentration of the excipient in the composition is 0 to 70%.

3. The lyophilizate composition according to claim 2, wherein the excipient is selected from the group consisting of mannitol, trehalose, sucrose and any combination thereof.

4. The lyophilizate composition according to claim 1, wherein said lyophilizate is sterile.

5. A dosage unit formulation comprising the lyophilizate composition of claim 1 in a container for reconstitution with a solvent thereby giving a solution of desired Mesna concentration.

6. The dosage unit formulation according to claim 5, wherein the lyophilizate composition comprises from 300 mg to 100 g of Mesna.

7. The dosage unit formulation according to claim 5, wherein the lyophilizate composition comprises from 3 g to 50 g of Mesna.

8. The dosage unit formulation according to claim 5, wherein said container is made of plastic or glass.

* * * * *